United States Patent
Ziche et al.

(10) Patent No.: US 6,855,684 B2
(45) Date of Patent: Feb. 15, 2005

(54) COMPOUND B AS ANGIOGENIC AGENT IN COMBINATION WITH HUMAN GROWTH FACTORS

(75) Inventors: Marina Ziche, Florence (IT); Silvia Donini, Rome (IT); Francesco Borrelli, Rome (IT)

(73) Assignee: Applied Research Systems ARS Holding N.V., Curacao (AN)

( * ) Notice: Subject to any disclaimer, the term of this patent is extended or adjusted under 35 U.S.C. 154(b) by 262 days.

(21) Appl. No.: 09/756,185

(22) Filed: Jan. 9, 2001

(65) Prior Publication Data

US 2001/0031733 A1 Oct. 18, 2001

Related U.S. Application Data

(63) Continuation of application No. PCT/EP99/04605, filed on Jul. 2, 1999.

(30) Foreign Application Priority Data

Jul. 9, 1998 (EP) .............................. 98112775

(51) Int. Cl.⁷ ........................ A01N 37/18; A61K 38/00; A61K 38/24; C07K 14/00

(52) U.S. Cl. .............................. 514/2; 514/12; 530/350; 530/399

(58) Field of Search ....................... 514/2, 12; 530/350, 530/399, 351

(56) References Cited

U.S. PATENT DOCUMENTS 5,998,364 A * 12/1999 Borrelli et al. ................ 514/2

FOREIGN PATENT DOCUMENTS

| WO | 94 14959 | 7/1994 |
| WO | 97 39765 | 10/1997 |

OTHER PUBLICATIONS

Folkman, "Clinical Application of Research on Angiogenesis", *Seminars in Medicine of the Beth Israel Hospital, Boston*, vol. 333, No. 26, pp. 1757–1763, Dec. 29, 1995.

* cited by examiner

*Primary Examiner*—Jon Weber
*Assistant Examiner*—Rita Mitra
(74) *Attorney, Agent, or Firm*—Browdy and Neimark, PLLC (57) ABSTRACT

The present invention refers to the use of Compound B as angiogenic agent in combination with human growth factors.

12 Claims, 10 Drawing Sheets

COMPOUND B AS ANGIOGENIC AGENT IN COMBINATION WITH HUMAN GROWTH FACTORS

The present application is a continuation of PCT/EP99/04605, filed 02 Jul. 1999.

FIELD OF THE INVENTION

The present invention refers to the use of Component B as angiogenic agent in combination with human growth factors.

State of the Art

Component B (hereinafter indicated as CB) is a 81 amino acid protein originally isolated from human urine. The human gene expressing the protein has been cloned and expressed in CHO cells as recombinant human Component B, the protein has a molecular weight of about 8.9 kD and was thoroughly described in WO 94/14259 to which reference is made also for the methods of preparation and its amino acid sequence.

In WO97/39765 the use of CB as cicatrizant was described.

It is also known that growth factors, as for example basic fibroblast growth factor (bFGF) or vascular endothelial growth factor (VEGF) have angiogenic activity.

BRIEF DESCRIPTION OF THE DRAWINGS

FIG. 1: Shows the implant of a pellet loaded with both active compounds (1A) or of two pellets each loaded with one active compound (1 B) in the rabbit cornea.

DETAILED DESCRIPTION OF THE INVENTION

It was now surprisingly found that the simultaneous presence of CB and a growth factor increases the angiogenic response elicited by either individual agent, in other words CB is capable of synergizing with a growth factor in promoting neovascular growth in the tissues probably facilitating some early events required to mobilise endothelial cells from capillaries.

Therefore, the main object of the present invention is the use of CB in combination with a growth factor for the manufacture of pharmaceutical compositions useful for the treatment of wounds, ulcers and other traumatic lesions to any of the tissues in the body.

Another object of the invention are pharmaceutical compositions prepared as described above.

A further object of this invention is a method of treatment of wounds, ulcers and other traumatic lesions to any of the tissues in the body, comprising administering an effective amount of CB and of a growth factor, possibly together with a pharmaceutically acceptable excipient.

The administration of the active ingredient may be oral, intravenous, intramuscular, subcutaneous or topical. Other routes of administration, which may establish the desired blood levels of respective active agents are comprised by the present invention.

The administration of the two active compounds can be performed by a single pharmaceutical preparation containing both of them or, preferably, by two pharmaceutical preparation each containing separately one of the two ingredients. Preferred growth factor to be used in combination with CB according to the invention are the basic fibroblast growth factor (bFGF) or the vascular endothelial growth factor (VEGF).

Angiogenesis was studied in the cornea of albino rabbits since this is an avascular and transparent tissue where inflammatory reactions and growing capillaries can be easily monitored and changes quantified by stereomicroscopic examination (Ziche et al., 1982). This method allows the monitoring over an extended period of time of vessel growth by direct and non traumatic observation of the process. Moreover in the same animal the quantification of the effect can be compared to that of a known agent.

The investigation of the role of Component B (CB) in in vivo angiogenesis studied in the rabbit cornea assay was performed by:
a) testing the ability of the molecule to produce vessel growth when placed into the avascular corneal stroma;
b) testing the ability of the molecule to favour or repress neovascularization elicited by the angiogenesis factor basic fibroblast growth factor (bFGF) or vascular endotelial growth factor (VEGF).

Methods

Protocol For Slow-release Preparation of Test Compounds

Growth factors or peptides were prepared as slow-release pellets.

Slow-release pellets (1×1×0.5 mm) were prepared in sterile conditions incorporating the test substances into a casting solution of a ethinyl-vinyl copolymer (Elvax-40, Dupont, Wilmington, Del.), in 10% methylene chloride (10 μl/droplet) (Langer and Folkman, 1976; Ziche et al. 1982).

Surgical Procedure

The angiogenic activity was assayed in vivo using the rabbit cornea assay.

In the lower half of New Zealand white rabbit eye (Charles River, Calco, Lecco, Italy), anaesthetised by sodium pentothal (30 mg/kg), a micro pocket (1.5×3 mm) was surgically produced using a pliable iris spatula 1.5 mm wide.

The pellets were implanted in the micropockets located into the transparent avascular corneal stroma.

Quantification of Corneal Angiogenesis

Subsequent daily observations of the implants were made with a slit lamp stereomicroscope without anaesthesia. An angiogenic response was scored positive when budding of vessels from the limbal plexus occurred after 3–4 days and capillaries progressed to reach the implanted pellet according to the scheme previously reported (Ziche et al. 1989). Angiogenic activity is expressed as the number of implants exhibiting neovascularization over the total implants studied. Potency is scored by the number of newly formed vessels and by their growth rate. Data are expressed as angiogenesis score, calculated as vessel density×distance from limbus in mm. A density value of 1 corresponded to 0 to 25 vessels per cornea, 2 from 25 to 50, 3 from 50 to 75, 4 from 75 to 100 and 5 for more than 100 vessels (Ziche et al., 1994).

Experimental Design

The Effect of Component B was Tested Following Two Procedures:

A) Three different concentrations of the molecule were tested in the cornea of at least 4 distinct rabbits per each dose, to define the potential angiogenic activity of the compound. The effect of Component B was compared with that elicited by the growth factor bFGF at 50 and 100 nag/pellet. In this experimental protocol rabbits were monitored for 3 weeks.

B) To evaluate a potential role of Component B in modulating angiogenesis the effect of this agent was tested in the presence of a defined angiogenesis factor, i.e. bFGF. To this aim two adjacent pockets were surgically produced in the same cornea, one bearing the angiogenic trigger and the other Component B. Experiments were also performed testing both substances incorporated into the same pellet (FIG. 1).

This last experimental protocol was specifically set up by our group to define:

1) the effect of the agent as a "costimulator" of the angiogenesis elicited by bFGF; or 2) the ability of the agent to inhibit angiogenesis elicited by the growth factor (Ziche et al, 1992 and 1994).

In this experimental protocol the rabbits were monitored for 4–5 weeks. The same protocol was used to tests the effect of CB as "costimulator" of the angiogenesis induced by VEGF.

Histological Analysis

Rabbit corneas with corneal pockets containing CB and/or bFGF were sampled at 2, 6, 15 days post surgery, and fixed in formalin after removing the pellets.

Routine histopathological processing was performed; sections 5 $\mu$m thick were cut next to where each pellet was placed; sections were stained with hematoxylineosin. At least 40 sections were examined per each cornea.

Statistical Analysis

Results are expressed as means for (n) implants. Angiogenic score data contained both positive and negative results. Multiple comparisons were performed by one-way ANOVA and individual differences were tested by Fisher's test after the demonstration of significant intergroup differences by ANOVA. A P value <0.05 was taken as significant (see also Appendix for further statistical evaluation).

Results a) Angiogenic Activity of CB

The angiogenic activity of CB was tested after incorporating increasing concentrations of the compound in slow release pellets of the polymer Elvax-40. Solubilization and incorporation of the compound into the polymer pellets did not cause any specific problem. The doses tested were: 0.2, 0.5, 2 and 4 pg/pellet. The effect of CB was compared to that produced by basic fibroblast growth factor (bFGF).

Figure 2A:
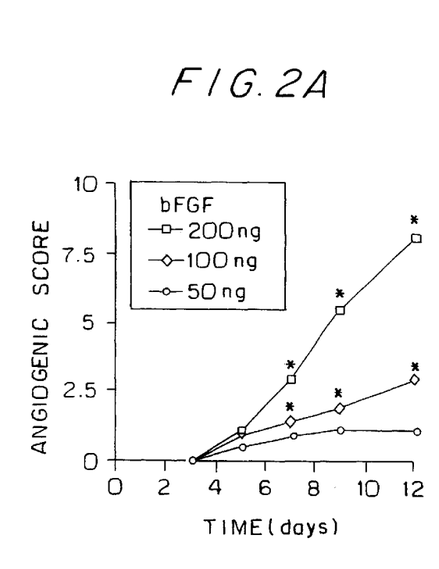
FIG. 2: Shows the effect of bFGF and CB on angiogenesis in the rabbit cornea.
Figure 2B:
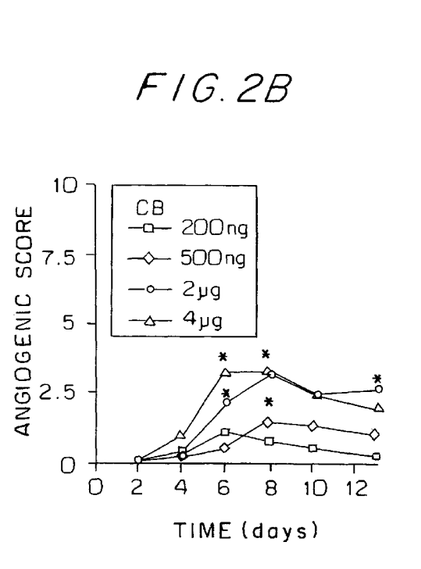

CB elicited a dose-dependent angiogenic effect whose potency appeared to be weaker than the one elicited by bFGF. In FIG. 2A data are reported on the angiogenic activity of bFGF obtained from previous experiments and from the experiments run in parallel with CB. In FIG. 2B data from daily observation of rabbit corneas implanted with CB-containing pellets are reported as angiogenic score. The highest angiogenic score obtained with CB averaged around 3–3.5 (2–4 $\mu$g/pellet) (P<0.05 vs vehicle pellets alone) vs 7–8 produced by bFGF (0.2 $\mu$g/pellet)(P<0.05 vs vehicle pellets alone). CB was not angiogenic at the concentration of 0.2 $\mu$g/pellet. As shown in Table 1, 0.5 $\mu$g/pellet CB induced a positive angiogenic response in 1 implant out of 5 performed. Two and 4 $\mu$g/pellet were the most effective doses. These doses induced a similar angiogenic activity and produced 2 positive implants out of 5 performed.

CB was devoid of any macroscopic inflammatory activity as revealed by the persistence of corneal transparency all through the experiments at any concentration tested.

Figure 3:
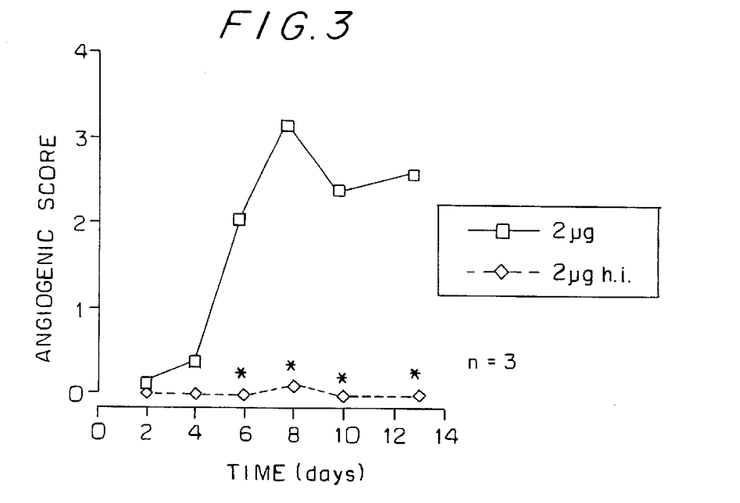
FIG. 3: Shows the effect of heat-inactivation on the angiogenic activity of CB.

To assess the specificity of CB angiogenic effect, the compound was heat-inactivated (h.i.) by boiling it for 20 min. The dose of 2 $\mu$g was then tested. Following heat inactivation CB completely lost angiogenic activity (FIG. 3)(P<0.05 vs CB 2 $\mu$g).

b) Effect of CB on the Angiogenesis Induced by bFGF

Figure 1A:
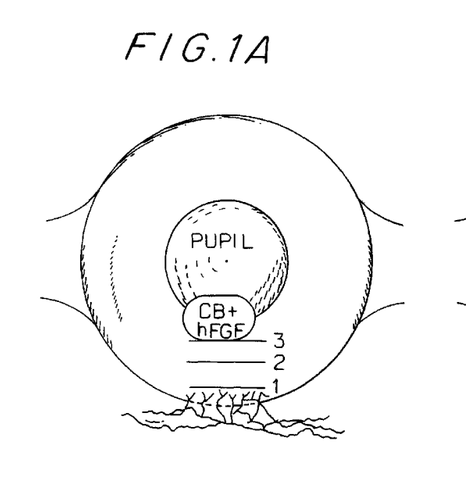
Figure 1B:
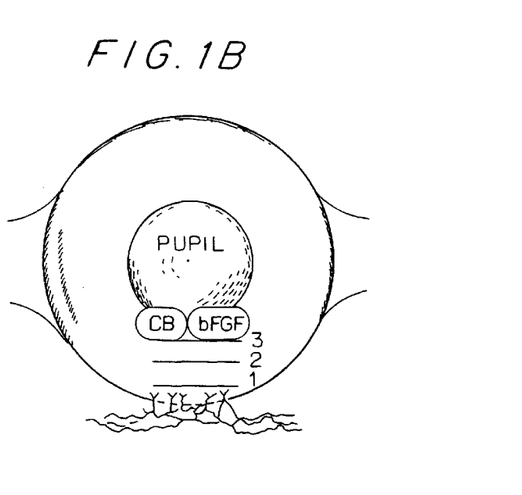

To evaluate the potential role of CB in modulating the effect of a known angiogenic effector, experiments were performed testing suboptimal concentrations of both substances (500 ng of CB and 100 ng of bFGF) co-released into the corneal stroma. Experiments were performed testing both substances incorporated into the same pellet (FIG. 1A). Furthermore the compounds were tested at the same concentration as above but released into the stroma separately in 2 independent pellets (FIG. 1B).

Figure 4A:
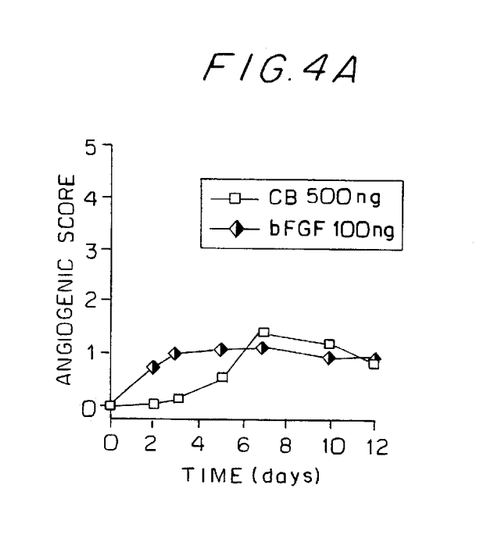
FIG. 4: Shows the synergistic effect of CB on bFGF-induced angiogenesis.
Figure 4B:
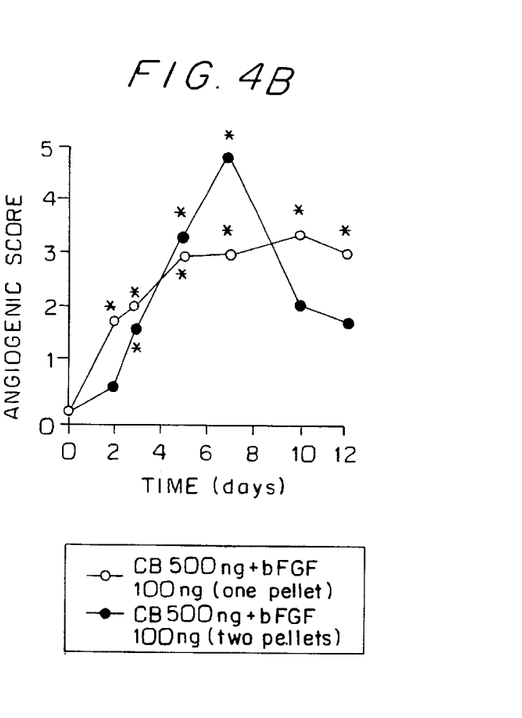

The simultaneous presence of CB and bFGF into the cornea increased the angiogenic response elicited by either individual agent (FIG. 4A and B, Table 2).

Angiogenesis occurred earlier and progressed more rapidly producing a significant increment of the number of newly formed vessels (P<0.05 vs CB and bFGF alone). This effect was apparent in both experimental conditions.

However, when CB and bFGF were released independently by 2 separate pellets the effect was higher. Capillaries grew toward bFGF rather than CB suggesting that CB contributed to potentiate bFGF activity. After 7 days, neovascular growth started to regress.

Figure 5A:
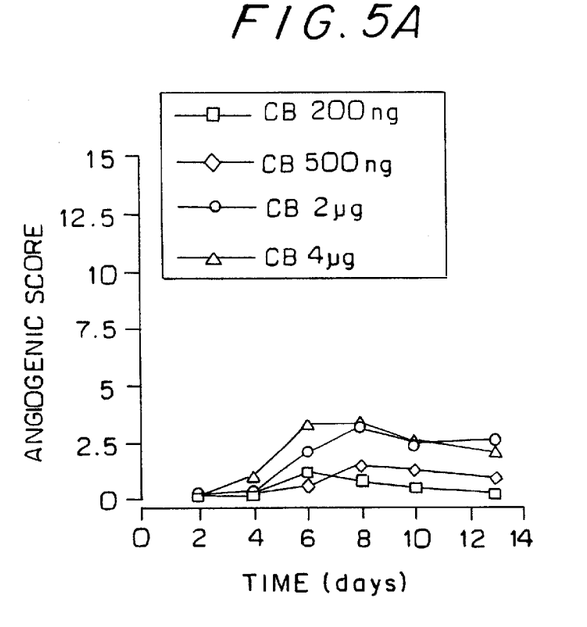
FIG. 5: Shows the synergistic effect of CB on the angiogenic activity of bFGF.
Figure 5B:
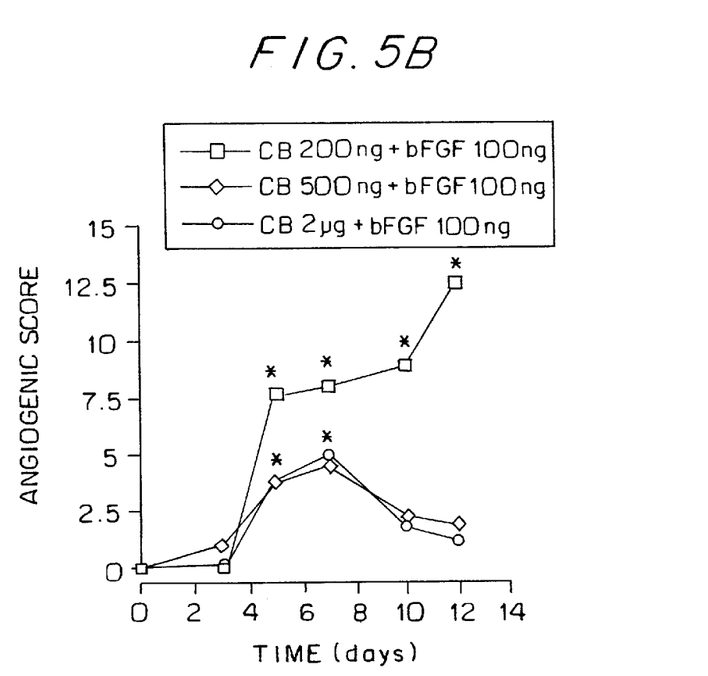
Figure 6:
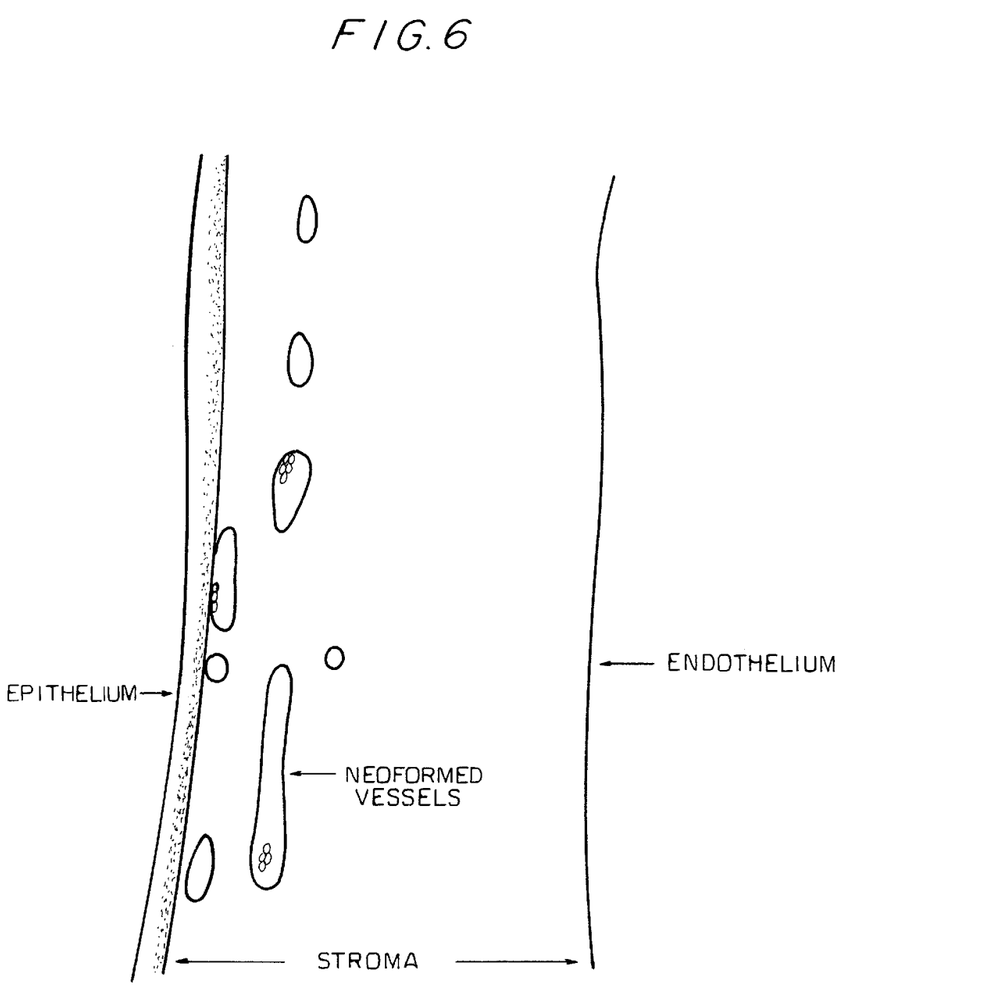
FIG. 6: Represents a drawing of a typical histological section of rabbit cornea illustrating the main structures observable in following FIGS. 7–11.

Additional experiments were performed with increasing concentrations of CB (0.2, 0.5 and 2 $\mu$g/pellet) on the angiogenesis elicited by a constant concentration of bFGF (100 ng). A synergism between the two molecules could be observed (FIG. 5). Interestingly, the most effective condition of synergism between CB and bFGF was observed with 200 ng CB (P<0.05 vs CB and bFGF alone) tested in two separate pellets.

c) Effect of CB on the Angiogenesis Induced by VEGF

In Table 3 the synergistic effect of Component B on VEGF-induced angiogenesis are reported.

The synergism between CB and VEGF was evaluated with the factors tested in two separate pellets. The results obtained at day 10 are reported in Table 3. The data are expressed as the number of implants exhibiting neovascularization with an angiogenesis score equal or over to 6, over the total implants performed. Further statistical analysis was performed in order to confirm possible positive interactions between the test compounds using a more conservative analysis (see FIG. 11 in Appendix).

The main factors ("test compounds" and "angiogenic score" over time) were analysed according to the Multifactor Analysis. The results showed that statistically significant differences (p<0.0001) are present among the test compounds over the time.

Figure 12:
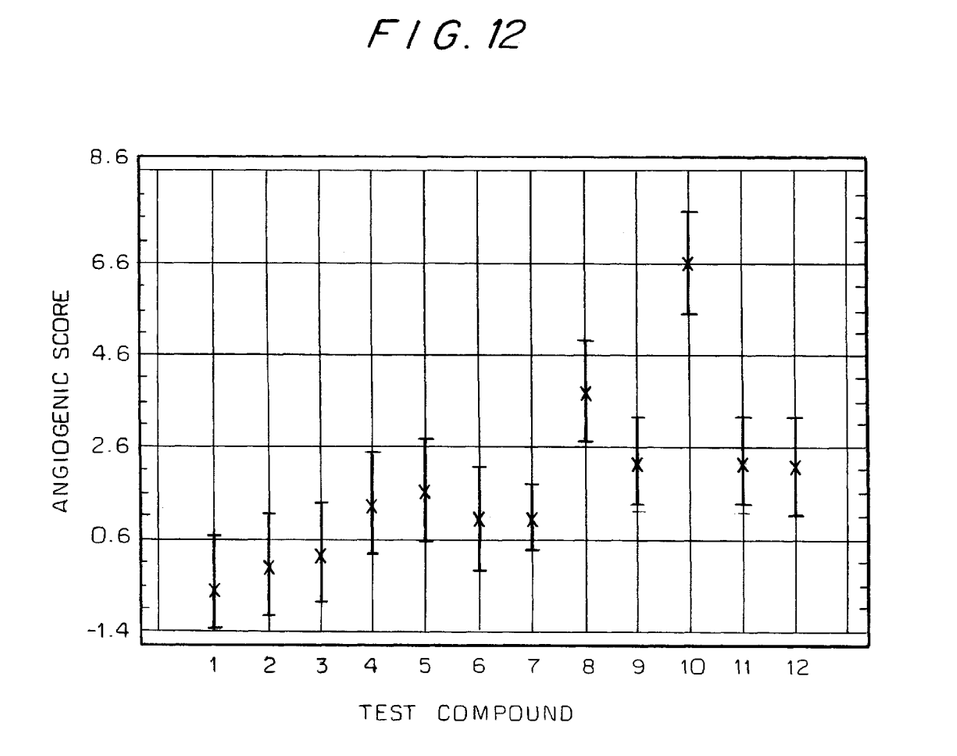
FIG. 12: mean and 95.0% Tukey HSD Intervals

As to the interaction among the test compounds the results of the Tukey's test allow the following considerations (see FIG. 12 below):

CB 500 ng+bFGF 100 ng (1 pellet)

Both compounds individually are not statistically different from controls. The combination of the two compounds gave a response which is statistically different from either the controls and the single drugs. The response is around the expected additive effect.

CB 200 ng+bFGF 100 ng (2 pellets)

Both compounds individually are not statistically different from controls. The combination of the two compounds gave a response which is statistically different from either the controls and the single drugs. In addition, it should be noted that the response of the combined treatments clearly exceeds the expected additive effect. The above seems to confirm the presence of a synergistic effect between the two drugs.

CB 500 ng+bFGF 100 ng (2 pellets)

Both compounds are not statistically different from controls. The combination of the two compounds gave a response which is statistically different either from the controls and the single drugs. The response is around the expected additive effect. In addition, no differences were found comparing CB 500 ng+bFGF 100 ng (1 pellet) vs CB 500 ng+bFGF 10 ng (2 pellet).

CB 2 $\mu$g+bFGF 100 ng (2 pellets)

Both compounds are not statistically different from controls. The combination of the two compounds gave a response which is statistically different from controls but not from the single compounds. The response is around the expected additive effect.

Histological Analysis

Figure 7:
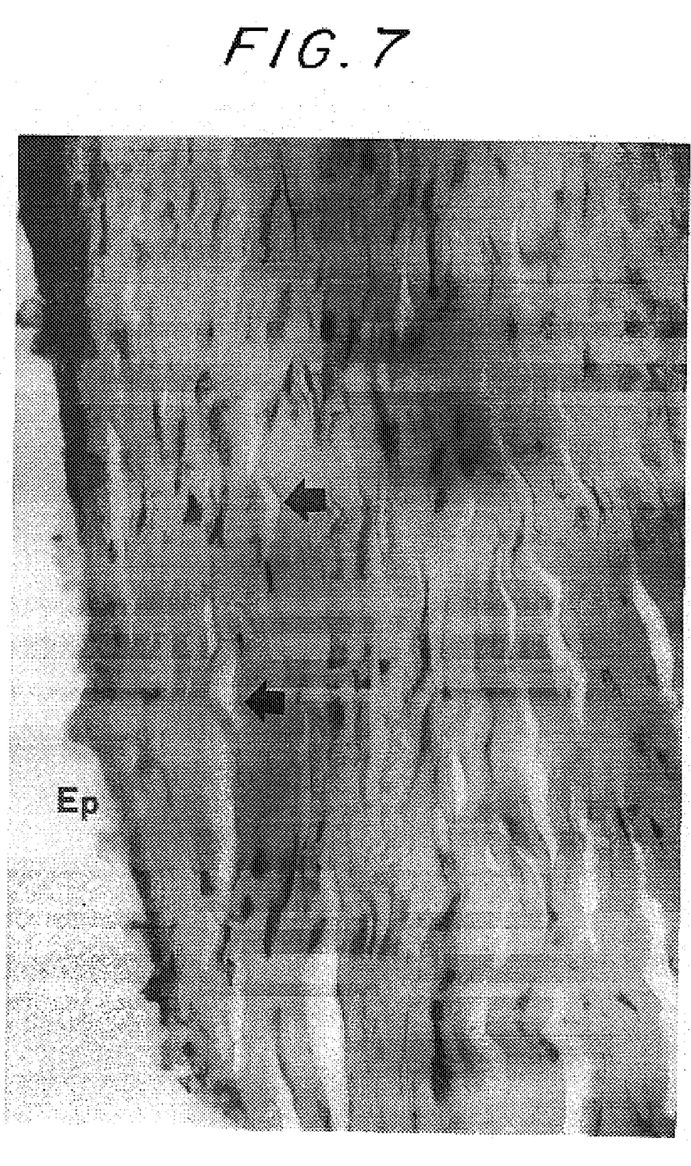
FIG. 7: section of rabbit cornea (×200) with a corneal pocket containing 100 ng of bFGF sampled at 6 days post-surgery wherein the arrows show neoformed vessels. (Ep=epithelium).
Figure 8:
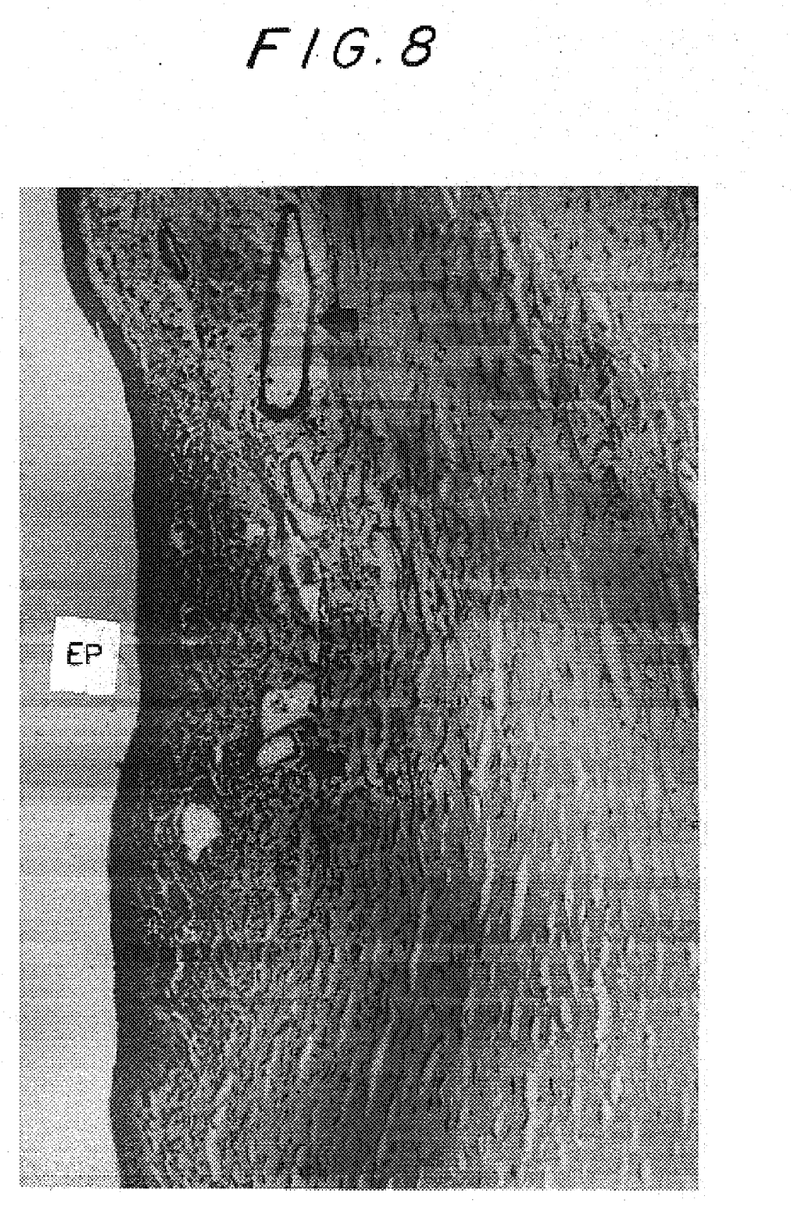
FIG. 8: section of rabbit cornea (×100) with a corneal pocket containing 500 ng of CB sampled at 2 days post-surgery wherein the arrows show neoformed vessels.
Figure 9:
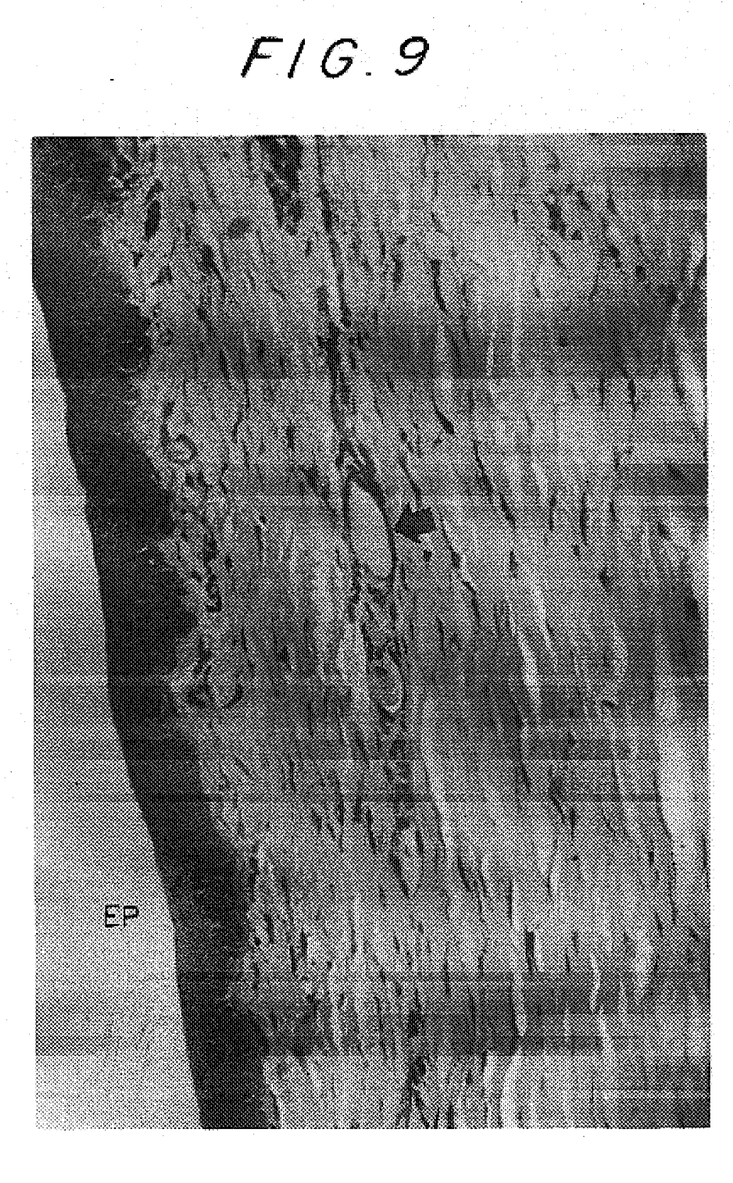
FIG. 9: section of rabbit cornea (×200) with a corneal pocket containing 500 ng of CB sampled at 6 days post-surgery wherein the arrows show neoformed vessels.
Figure 10:
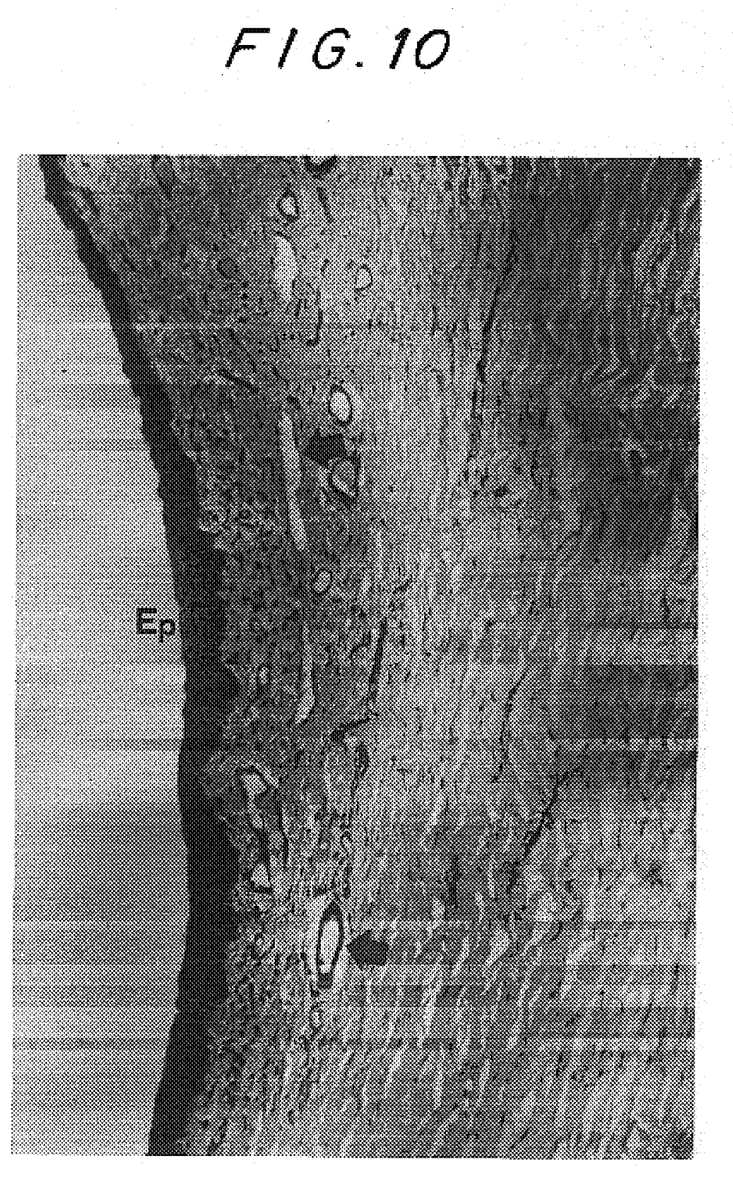
FIG. 10: Section of rabbit cornea (×100) with a corneal pocket containing 4 μg of CB sampled at 15 days post-surgery wherein the arrow show neoformed vessels.
Figure 11:
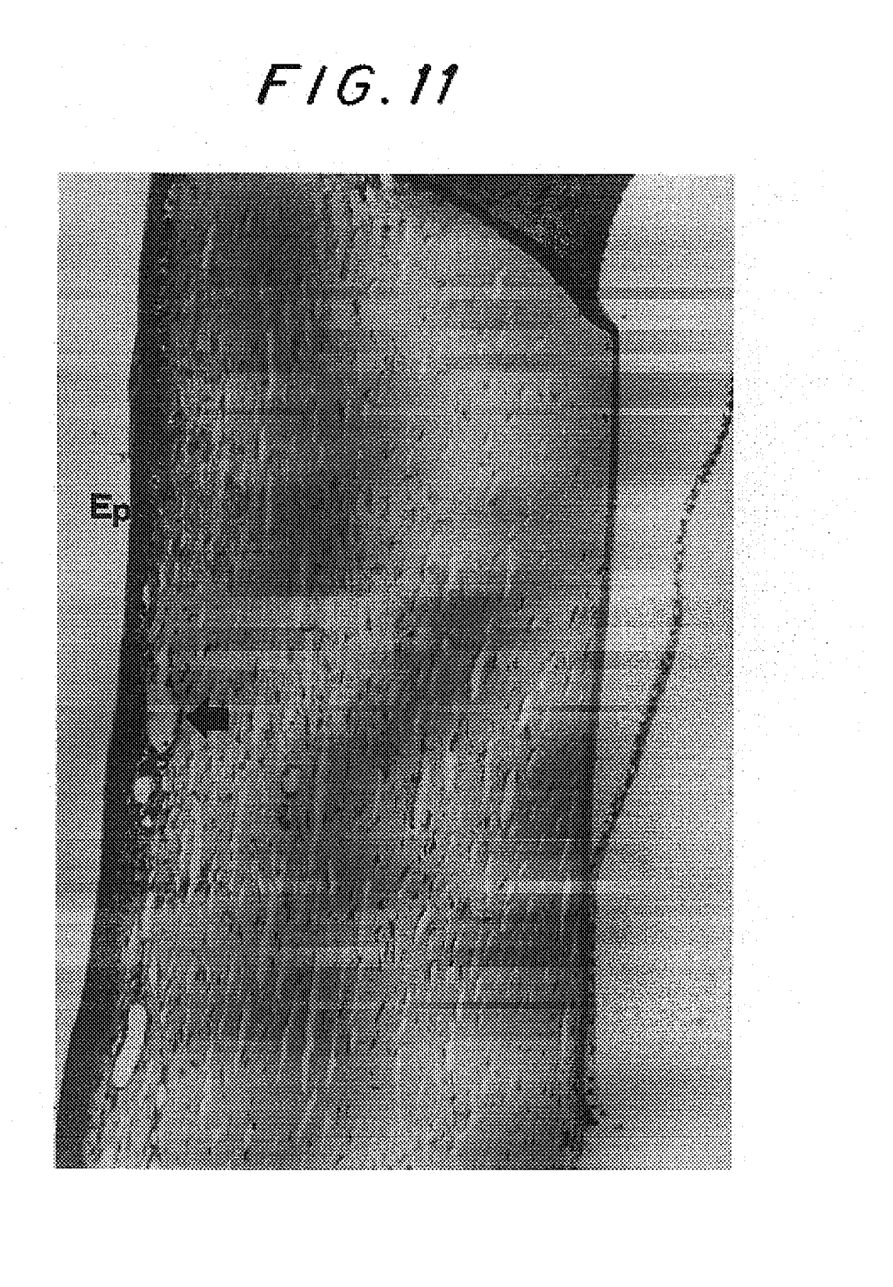
FIG. 11: Section of rabbit cornea (×100) with a corneal pocket containing 500 ng of bFGF sampled at 15 days post-surgery wherein the arrow show neoformed vessels.

The effect of CB was examined at the maximal effective concentration (4 $\mu$g) and at a suboptimal concentration (500 ng) in the presence and in the absence of bFGF (100 ng). No difference in the extent of cellular infiltrate was apparent between CB and bFGF implants in any combination (FIGS. 7,8,9). Within 2 days from the implants a leukocyte infiltrate surrounded a dense network of newly formed capillaries in proximity of the limbal region at the epithelial side of the cornea (FIG. 10). At day 6 a consistent reduction in the extent of the leukocyte infiltrate was apparent while capillary vessels appeared increased in number and caliber in response to either molecule (FIG. 11). At day 15 the extent of the leukocyte infiltrate was negligible while capillaries appeared morphologically unmodified.

Conclusions

Component B possesses angiogenic activity which is apparent in the concentration range of micrograms and which is lost by heat inactivation. Most of the angiogenesis factors are angiogenic at concentrations 20–40 fold lower. Together with the high concentration required to elicit angiogenesis, 2 aspects appear relevant in CB effect:

1) the ability to elicit budding of capillaries within the first 3–4 days from the implant, mimicking the secreted angiogenesis factor VEGF rather than the matrix linked angiogenesis factor bFGF;
2) the flattening over time of the efficiency of neovascular growth, leading to only 30–40% of the implant tested to be fully vascularized after 10–14 days. Our results indicate that CB induces angiogenesis in vivo and has the ability to synergize with bFGF in promoting neovascular growth in the rabbit cornea.

These considerations together with the characteristics of the potentiation of the angiogenic response in the presence of bFGF, suggest that CB requires the presence of additional growth factors to fully express its angiogenic potential in vivo.

Histological examination of corneal sections sampled at various time intervals was performed to assess whether the angiogenesis process elicited by CB involved inflammatory cell infiltrate. The effect of CB was compared to that produced by the corneal implant of bFGF. At routine histological examination we did not find major differences in the extent and in the type of leukocyte infiltrate in corneas receiving CB, bFGF or the combination of the two. Thus from our results we can conclude that the corneal vascularization induced by CB does not appear to be mediated by gross inflammatory reaction products since no sign of corneal opacity was apparent.

The characteristic of the angiogenic response elicited in the avascular cornea by CB suggests that CB might facilitate some of the early events required to mobilise endothelial cells from capillaries. Once this process is started and endothelial cells are "loosened" from the tight boundary to the extracellular matrix, bFGF expresses its mitogenic effect with more efficiency.

TABLE 1

Effect of Component B on angiogenesis in the rabbit cornea

| CB ($\mu$g/pellet) | Positive implants/total performed | bFGF (ng/pellet) | Positive implants/total performed |
|---|---|---|---|
| 0 | 0/6 | 0 | 0/6 |
| 0.2 | 0/5 | 50 | 1/6 |
| 0.5 | 1/5 | 100 | 2/6 |
| 2 | 2/5 | 200 | 5/6 |
| 4 | 2/5 | | |

TABLE 2

Synergistic effect of Component B on bFGF-induced angiogenesis

| Test compounds | Positive implants/total performed |
|---|---|
| CB 500 ng | 1/5 |
| bFGF 100 ng | 1/5 |
| CB 500 ng + bFGF 100 ng (one pellet) | 3/6 |
| CB 500 ng + bFGF 100 ng (two pellets) | 4/5 |

TABLE 3

Synergistic effect of Component B on VEGF-induces angiogenesis

| | Positive implants/total performed |
|---|---|
| CB 200 ng | 0/5 |
| CB 500 ng | 1/5 |
| VEGF 100 ng | 1/4 |
| CB 200 ng + VEGF 100 ng | 2/4 |
| CB 400 ng + VEGF 100 ng | 4/4 |

What is claimed is:

1. A pharmaceutical composition for promoting angiogenesis, comprising Component B and a human growth factor selected from the group consisting of bFGF and VEGF, in combination with a pharmaceutically acceptable carrier, wherein the ratio of the amount of said Component B to the amount of said human growth factor is selected to provide synergistic angiogenesis results when administered to a patient in need thereof.

2. A method for promoting angiogenesis in a patient in need thereof, comprising administering to the patient Component B and a human growth factor selected from the group consisting of bFGF and VEGF, for a time sufficient and in amounts effective for the promotion of angiogenesis in the patient, wherein said Component B and said human growth factor are administered such that they will be simultaneously present in the blood of the patient in amounts effective for the synergistic promotion of angiogenesis in the patient.

3. The method of claim 2, wherein the angiogenesis is in relation to the treatment of a wound, ulcer or other traumatic lesion to the tissues of the body of the patient.

4. The method of claim 2, wherein the Component B and the human growth factor are administered in a single composition.

5. The method of claim 3, wherein the Component B and the human growth factor are administered in a single composition.

6. The method of claim 2, wherein the Component B and the human growth factor are administered in separate compositions.

7. The method of claim 3, wherein the Component B and the human growth factor are administered in separate compositions.

8. The method of claim 2, wherein the ratio of the amount of Component B to the amount of the human growth factor is selected to provide synergistic angiogenesis results.

9. A pharmaceutical composition for treating a wound, ulcer, or other traumatic lesion, comprising Component B and a human growth factor selected from the group consisting of bFGF and VEGF, in combination with a pharmaceutically acceptable carrier, wherein the ratio of the amount of said Component B to the amount of said human growth factor is selected to provide synergistic results when administered to a patient in need thereof.

10. A method of treating a wound, ulcer, or other traumatic lesion in a patient in need thereof, comprising administering the patient Component B and a human growth factor selected from the group consisting of bFGF and VEGF, for a time sufficient and in an amount effective for the treatment of the wound, ulcer or other traumatic lesion in the patient, wherein said Component B and said human growth factor are administered such that they will be simultaneously present in the blood of the patient in amounts effective for the synergistic treatment of the wound, ulcer or other traumatic lesion in the patient.

11. The method of claim 10, wherein the Component B and the human growth factor are administered in separate administration doses.

12. The method of claim 10, wherein the ratio of the amount of Component B to the amount of the human growth factor is selected to provide synergistic results.

* * * * *